United States Patent [19]

Cheng

[11] Patent Number: 5,445,159
[45] Date of Patent: Aug. 29, 1995

[54] MINIMALLY INVASIVE METHOD TO DETERMINE THE LEFT VENTRICULAR PRESSURE WAVEFORM

[76] Inventor: Wang Cheng, 1619 84 St., Brooklyn, N.Y. 11214

[21] Appl. No.: 342,707

[22] Filed: Nov. 21, 1994

[51] Int. Cl.⁶ .............................................. A61B 5/021
[52] U.S. Cl. .................................. 128/672; 128/700; 364/413.03
[58] Field of Search ............... 128/696, 695, 672, 700, 128/673, 687; 364/413.03, 413.05

[56] References Cited

U.S. PATENT DOCUMENTS

| | | | |
|---|---|---|---|
| 4,651,747 | 3/1987 | Link | 128/672 |
| 5,099,852 | 3/1992 | Meister et al. | 128/672 |
| 5,265,011 | 11/1993 | O'Rourke | 128/672 |

Primary Examiner—William E. Kamm
Assistant Examiner—Kennedy J. Schaetzle

[57] ABSTRACT

A method for determining a patient's left ventricular pressure waveform without placement of a catheter inside the left ventricle, including converting the patient's ejection phase waveform of the peripheral arterial pressure by using a standardized ejection correlation curve, and converting the filling phase waveform of the pulmonary capillary wedge pressure by using a standardized filling correlation curve, into two portions of the left ventricular pressure waveform, and then connecting the two portions together with two straight lines to complete the left ventricular pressure waveform.

17 Claims, 2 Drawing Sheets

FORMATION OF EJECTION CORRELATION CURVE

LEFT VENTRICULAR PRESSURE WAVEFORM

FORMATION OF EJECTION CORRELATION CURVE

MINIMALLY INVASIVE METHOD TO DETERMINE THE LEFT VENTRICULAR PRESSURE WAVEFORM

CROSS-REFERENCE TO RELATED APPLICATION

This application is a substitute of application Ser. No. 07/888,336, filed May 22, 1992, now abandoned.

BACKGROUND OF THE INVENTION

1. Field of the Invention

The present invention relates to a minimally invasive method of determining a patient's left ventricular pressure waveform without placement of a catheter inside the left ventricle. More specifically, the present invention utilizes a computer to convert the patient's ejection phase waveform of the peripheral arterial pressure, and the filling phase waveform of the pulmonary capillary wedge pressure into portions of the left ventricular pressure waveform. These portions are then connected together to complete the left ventricular pressure waveform.

2. Prior Art

A plot or loop showing the left ventricular pressure to volume relationship has been believed to be one of the best parameters reflecting a patient's cardiac function. This left ventricular pressure to volume relationship loop consists of the left ventricular pressure waveform and the left ventricular volume waveform. Although a non-invasive left ventricular volume waveform can be obtained by radionuclide angiocardiography or echocardiography, a non-invasive left ventricular pressure to volume relationship loop is not available, due to the inability to measure the left ventricular pressure waveform by a non-invasive or minimally invasive method.

Dr. Cemil M. Puruts reported a method that required a radionuclide angiocardiography and an invasive method, placing a catheter into the left ventricle during cardiac surgery, to obtain a left ventricular pressure to volume relationship loop (The Journal of Nuclear Medicine 1988, 29:1492–1497).

In Daniel Bogen and Krishanu Gupta's method, an end-systolic pressure-volume relationship was measured by intraaortic balloon occlusion (U.S. Pat. No. 4,877,035, issued on Oct. 31, 1989). There are two differences between Bogen and Gupta's method and the present invention. First, Bogen and Gupta's method utilized a catheter in the arterial system, where the present invention utilizes a catheter in the venous system, thus making it less dangerous. Second, the minimally invasive method of the present invention can obtain an entire left ventricular pressure waveform, instead of just the end-systolic pressure point.

Joseph J. Panico found a non-invasive method to determine left ventricular end diastolic pressure by data processing analysis of the EKG waveform, first heart sound and carotid pulse waveform (U.S. Pat. No. 4,203,451, issued May 20, 1980). The method of the present invention uses the pulmonary capillary wedge pressure waveform to construct a full filling phase waveform of the left ventricular pressure, which is a closer physiologic property.

William T. Link's method obtained the systolic blood pressure by the diastolic blood pressure, arterial curve or amplitude curve and a different assumed systolic pressure (U.S. Pat. No. 4,564,020, issued on Jan. 14, 1986). Link's method did not involve the establishment of a left ventricular pressure waveform.

Thus, no minimally invasive method of determining the left ventricular pressure waveform is known at present.

SUMMARY OF THE INVENTION

The principal object of the present invention is to provide a minimally invasive method that can determine a patient's left ventricular pressure waveform without placement of a catheter inside the left ventricle.

A left ventricular pressure waveform in a heart cycle has four phases: (1) an ejection phase, (2) an isovolumetric relaxation phase, (3) a filling phase and (4) an isovolumetric contraction phase. The peripheral arterial pressure has an ejection phase waveform somewhat similar to the ejection phase waveform of the left ventricular pressure, and the pulmonary capillary wedge pressure is equal to the mean filling pressure of the left ventricular pressure. Both the isovolumetric relaxation phase waveform and the isovolumetric contraction phase waveform of the left ventricular pressure are virtually two straight lines.

In a first step, the electrocardiograph (EKG), peripheral arterial pressure waveform, pulmonary small arterial pressure waveform, pulmonary capillary wedge waveform and the left ventricular pressure waveform, from a sufficient number of persons or human subjects, are recorded simultaneously and digitized by a physiological recorder, an analog/digital convertor, and a PC computer provided with a data acquisition software and a spreadsheet software.

The recorded left ventricular pressure waveforms are divided into the four phases mentioned above. In a normal human subject, the start and the end of the ejection phase of the left ventricular pressure are determined to be the start of the ejection and the dicrotic notch of the peripheral arterial pressure, respectively. The start and end of the filling phase of the left ventricular pressure are determined to be the dicrotic notch of the pulmonary small arterial pressure and a point obtained 25–29 msec after the EKG Q wave, respectively. An ejection correlation curve is formed by multiplying the ejection phase waveform of the peripheral arterial pressure by the ejection phase waveform of the left ventricular pressure. A filling correlation curve is formed by multiplying the filling phase waveform of the pulmonary capillary wedge pressure by the filling phase waveform of the left ventricular pressure.

In a second step, a patient's EKG, peripheral arterial pressure waveform, pulmonary small arterial pressure waveform and pulmonary capillary wedge pressure waveform are recorded and digitized by the same methods used in the above first step. The patient's peripheral arterial pressure waveform and pulmonary arterial wedge pressure waveform are also separated into the ejection and filling phases, respectively. Standardized ejection and filling correlation curves, obtained from a predetermined number of human subjects in the first step, are then divided by the patient's ejection phase waveform of the peripheral arterial pressure and the filling phase waveform of the pulmonary capillary wedge pressure, respectively, to obtain the patient's ejection phase waveform and filling phase waveform of the left ventricular pressure. Then, the isovolumetric contraction and isovolumetric relaxation phases of the left ventricular pressure waveform are formed by two straight lines connecting the constructed ejection and filling phase waveforms, thus completing an entire left ventricular pressure waveform.

DETAILED DESCRIPTION OF THE PREFERRED EMBODIMENT

First, it is noted that the present invention uses the following equipment:

A. Catheters comprising the tip micromanometer, fluid-filled and Swan-Ganz catheters.

B. Physiological recorder having at least four channels with one EKG channel, and an oscilloscope display screen.

C. DT2801-A Model Analog and Digital I/O System that is available commercially from Data Translation, Inc., 100 Locke Drive, Marlborough, Mass. 01752, having at least four channels.

D. IBM compatible personal computer, such as the Gateway 2000 386/33 mHz computer system with at least 80 mB of memory and mathematic processor, which is available commercially from Gateway 2000, Corp., 610 Gateway Drive, North Sioux City, S. Dak. 57049, provided with a data acquisition software, Note-Book 6.1.2, that is available commercially from Laboratory Technologies Corp., 400 Research Drive, Wilmington, Mass. 01887, and a spreadsheet software, Excel 3.0, that is available commercially from Microsoft Corporation, One Microsoft Way, Redmond, Wash. 98052-6399.

Figure 1:
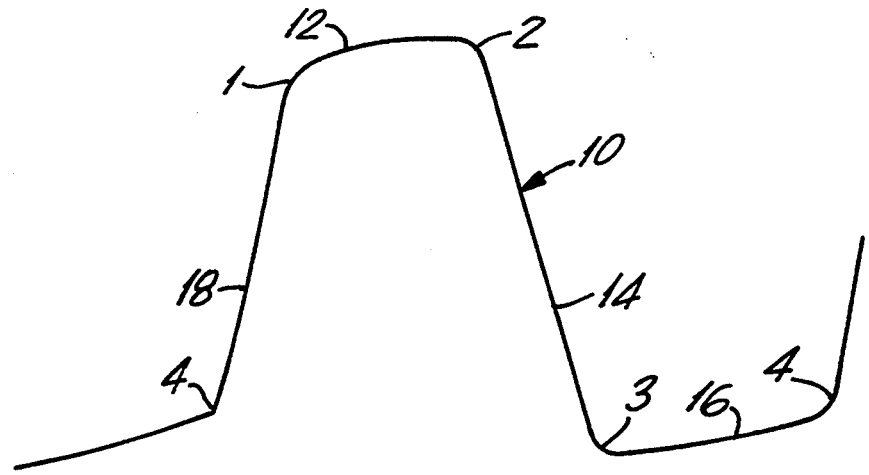
FIG. 1 shows a left ventricular pressure waveform that is separated into four phases.
Figure 2:
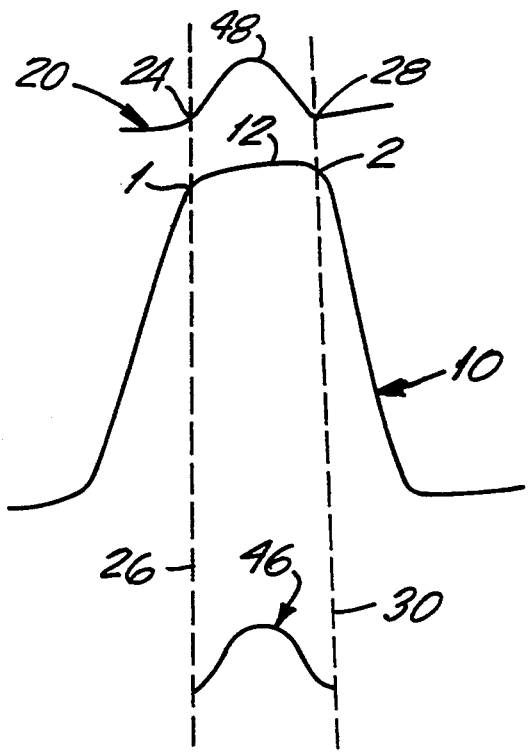
FIG. 2 shows the ejection phase and the formation of an ejection correlation curve.

Referring now to the drawings, FIG. 1 shows a left ventricular pressure waveform 10 in a heart cycle having four phases: an ejection phase 12, an isovolumetric relaxation phase 14, a filling phase 16 and an isovolumetric contraction phase 18, which are separated into waveforms designated in the drawings with the same numerals. On the one hand, the peripheral arterial pressure, such as in the carotid or femoral artery, has an ejection phase waveform somewhat similar to the ejection phase waveform of the left ventricular pressure. This is due to that, when the aortic valves open and the mitral valves close during the ejection phase, an open communicating system is formed from the left ventricle, through the aorta, and the peripheral artery. Therefore, the ejection phase waveform of the peripheral arterial pressure can reflect the ejection phase waveform of the left ventricular pressure, as set forth below. The peripheral arterial pressure waveform 20 is shown in FIG. 2.

Figure 3:
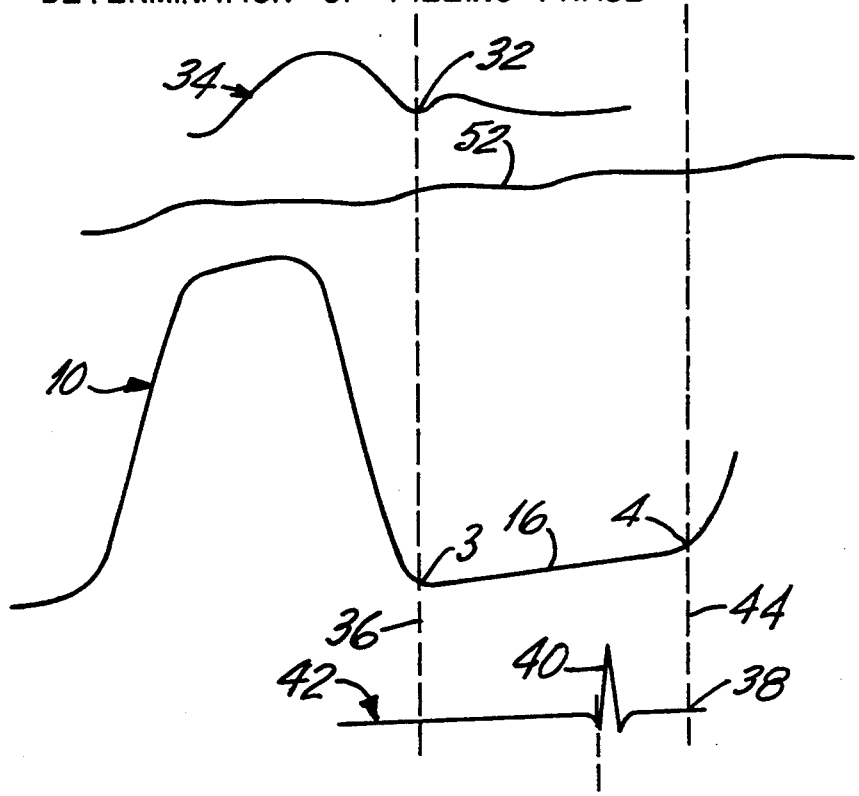
FIG. 3 shows the filling phase.
Figure 4:
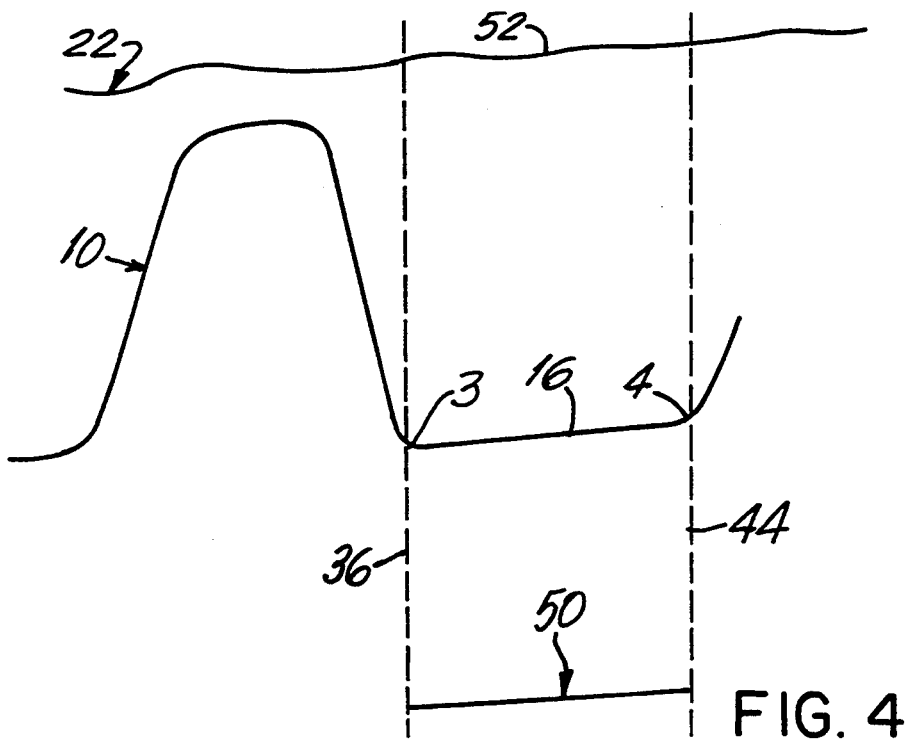
FIG. 4 shows the formation of a filling correlation curve.

On the other hand, the pulmonary capillary wedge pressure is equal to the mean filling pressure in the left ventricle. This is due to that, when the mitral valves open while the aortic valves close during the filling phase, an open communicating system is formed from the pulmonary capillary, through the pulmonary vein, the left atrium, and the left ventricle. The pulmonary capillary wedge pressure waveform 22 is shown in FIGS. 3 and 4. Both waveforms of the isovolumetric relaxation phase 14 and the isovolumetric contraction phase 18 of the left ventricular pressure are virtually two straight lines.

There are two steps for the application of this method. In the first step, two types of correlation curves have to be formed and stored. A person's EKG, peripheral arterial pressure waveform, pulmonary small arterial pressure waveform, pulmonary capillary wedge pressure waveform and the left ventricular pressure waveform are recorded simultaneously in a catheterization laboratory. Electric pads are placed on the body surface to record an EKG. A non-invasive cuff monitor or a minimally invasive arterial puncture to receive conventional means is used to obtain the peripheral arterial blood pressure. A multiple porus Swan-Ganz catheter is placed in the pulmonary capillary "wedge" position from a peripheral vein to obtain both pulmonary small arterial pressure and pulmonary capillary wedge pressure. A pigtail catheter is placed in the left ventricle from a peripheral artery to obtain the left ventricular pressure.

The transducers that connect with the above catheters and EKG are plugged into a physiological recorder with multiple channels. The output from this physiological recorder is transferred to a PC computer via an analog/digital convertor (i.e. DT2801-A). This PC computer has a data acquisition software, such as Notebook 6.1.2. (Labtech), and a spreadsheet software, such as Excel 3.0 (Microsoft). After the data are acquired with at least 150 Hz and digitized, if a time channel is designed on the file of the data acquisition software, six digitized waveforms are displayed by the spreadsheet software. The six digitized waveforms are time, left ventricular pressure, peripheral arterial pressure, pulmonary small arterial pressure, pulmonary capillary wedge pressure and EKG.

The left ventricular pressure waveform 10 is divided into four sections for the respective four phases 12, 14, 16 and 18 shown in FIG. 1. In a normal human subject with a normal heart rate, the start at point 1 and the end at point 2 of the ejection phase 12 of the left ventricular pressure waveform 10 are determined by a time period extending from the start 24 of the ejection, indicated by the broken time line 26, and the dicrotic notch 28 of the peripheral arterial pressure waveform 20, indicated by the broken time line 30, respectively, as shown in FIG. 2. The start at point 3 and the end at point 4 of the filling phase 16 of the left ventricular pressure waveform 10 are determined by a time period extending from the dicrotic notch 32 of the pulmonary small arterial pressure waveform 34, indicated by the broken time line 36, and a point 38 which is 25–29 msec after the Q wave 40 of the EKG 42, as indicated by the broken time line 44, respectively, as shown in FIG. 3. The determination of these four points also can be achieved by the techniques comprising echo-Doppler-cardiography, radionuclide angiocardiography, phonocardiography, ballistocardiography, peripheral arterial pressure waveform, pressure waveforms from right heart catheterization, pacemaker recording or EKG, or any combination of them.

With the spreadsheet software, an ejection correlation curve 46, as shown in FIG. 2, is formed by multiplying the ejection phase waveform 48 of the peripheral arterial pressure 20 (designed with the same numeral as the waveform thereof) by the ejection phase waveform 12 of the left ventricular pressure 10 (designated with the same numeral as the waveform thereof). The ejection phases of the pressure waveform of the different peripheral arteries have different timing constants to match the ejection phase 12 of the left ventricular pressure, due to the different distance between each peripheral artery and the aortic valve. A filling correlation curve 50, shown in FIG. 4, is formed by multiplying the filling phase waveform 52 of the pulmonary capillary wedge pressure 22 (designated with the same numeral as the waveform thereof), disposed between the broken time lines 36 and 44, by the filling phase waveform 16 of the left ventricular pressure 10, as shown in FIGS. 3 and 4. According to the statistical requirement, a sufficient number of the human subjects must be measured to obtain the two types of standardized correlation curves. These curves are stored, sorted, and standardized according to age, sex, heart rate, type of disease, severity of the disease, and the like.

In the second step, a patient's EKG, peripheral arterial pressure waveform, pulmonary small arterial pressure waveform and pulmonary capillary wedge pressure waveform are recorded simultaneously and digitized by a PC computer data acquisition software via a physiological recorder and an analog/digital convertor. With the spreadsheet software, the patient's peripheral arterial pressure waveform 20 and pulmonary capillary wedge pressure waveform 22 are separated into the ejection and filling phases 48, 52, respectively, by the methods mentioned above. A corresponding standard ejection correlation curve 46, obtained in the first step, is selected and divided by the patient's ejection phase waveform 48 of the peripheral arterial pressure 20, to obtain the patient's ejection phase waveform 12 of the left ventricular pressure 10. A standard filling correlation curve 50, also obtained in the first step, is selected and divided by the patient's filling phase waveform 52 of the pulmonary capillary wedge pressure 22, to obtain the patient's filling phase waveform 16 of the left ventricular pressure 10. Then, the isovolumetric contraction and isovolumetric relaxation phase waveforms 18, 14 of the left ventricular pressure 10 will be formed with two straight lines connecting point 4 to point 1, and point 2 to point 3, completing an entire left ventricular pressure waveform 10, as shown in FIG. 1.

In the first step, the ejection and filling correlation curves 46, 50 also can be formed by dividing the ejection and filling phase waveforms 12, 16 of the left ventricular pressure 10 by the ejection and filling phase waveforms 48, 52 of the peripheral arterial pressure 20 and the pulmonary capillary wedge pressure 22, respectively. In the second step, a patient's ejection and filling phase waveforms 48, 52 of the peripheral arterial pressure 20 and the pulmonary capillary wedge pressure 22 can be multiplied by the standard ejection and filling correlation curves 46, 50, respectively, to obtain the patient's ejection phase waveform 12 and filling phase waveform 16 of the left ventricular pressure 10.

What I claim is:

1. A minimally invasive method of determining a patient's left ventricular pressure waveform without placement of a catheter inside the left ventricle, said method comprising the steps of:

recording and digitizing a human subject's EKG, peripheral arterial pressure waveform, pulmonary small arterial pressure waveform, pulmonary capillary wedge pressure waveform, and left ventricular pressure waveform;

separating said left ventricular pressure waveform into an ejection phase waveform, an isovolumetric relaxation phase waveform, a filling phase waveform and an isovolumetric contraction phase waveform;

separating said peripheral arterial pressure waveform to obtain an ejection phase waveform;

a first factoring step utilizing said ejection phase waveform of said peripheral arterial pressure waveform and said ejection phase waveform of said left ventricular pressure waveform to form an ejection correlation curve;

separating said pulmonary capillary wedge pressure waveform to obtain a filling phase waveform;

a second factoring step utilizing said filling phase waveform of said pulmonary capillary wedge pressure waveform and said filling phase waveform of said left ventricular pressure waveform to form a filling correlation curve;

storing, sorting and standardizing said ejection and filling correlation curves obtained from a predetermined number of human subjects to provide standardized ejection and filling correlation curves;

recording and digitizing a patient's EKG, peripheral arterial pressure waveform, pulmonary small arterial pressure waveform and pulmonary capillary wedge pressure waveform;

separating said peripheral arterial pressure waveform of said patient to obtain an ejection phase waveform of said patient;

a third factoring step utilizing said standardized ejection correlation curve and said ejection phase waveform of said patient to form an ejection phase waveform of a left ventricular pressure of said patient;

separating said pulmonary capillary wedge pressure waveform of said patient to obtain a filling phase waveform of said patient;

a fourth factoring step utilizing said standardized filling correlation curve and said filling phase waveform of said patient to form a filling phase waveform of the left ventricular pressure of said patient; and connecting said ejection and filling phase waveforms of the left ventricular pressure of the patient with two straight lines, one of said straight lines representing said patient's isovolumetric relaxation phase waveform and the other of said straight lines representing the patient's isovolumetric contraction phase waveform to complete a left ventricular pressure waveform of said patient.

2. A minimally invasive method according to claim 1, wherein said first factoring step includes multiplying said ejection phase waveform of said peripheral arterial pressure waveform of said human subject by said ejection phase waveform of said left ventricular pressure waveform of said human subject;

said second factoring step includes multiplying said filling phase waveform of said pulmonary capillary wedge pressure waveform of said human subject by said filling phase waveform of said left ventricular pressure waveform of said human subject;

said third factoring step includes dividing said standardized ejection correlation curve by said ejection phase waveform of said peripheral arterial pressure waveform of said patient; and said fourth factoring step includes dividing said standardized filling correlation curve by said filling phase waveform of said pulmonary capillary wedge pressure waveform of said patient.

3. A minimally invasive method according to claim 1, wherein said first factoring step includes dividing said ejection phase waveform of said left ventricular pressure waveform of said human subject by said ejection phase waveform of said peripheral arterial pressure waveform of said human subject;

said second factoring step includes dividing said filling phase waveform of said left ventricular pressure waveform of said human subject by said filling phase waveform of said pulmonary capillary wedge pressure waveform of said human subject;

said third factoring step includes multiplying said standardized ejection correlation curve by said ejection phase waveform of said peripheral arterial pressure waveform of said patient; and said fourth factoring step includes multiplying said standardized filling correlation curve by said filling phase waveform of said pulmonary capillary wedge pressure waveform of said patient.

4. A minimally invasive method according to claim 1, wherein each of said ejection phase waveforms is determined by a time period extending from a start-of-ejection point to a dicrotic notch of said peripheral arterial pressure waveform.

5. A minimally invasive method according to claim 1, wherein each of said filling phase waveforms is determined by a time period extending from a dicrotic notch of said pulmonary small arterial pressure waveform to a point disposed 25–29 msec after a Q wave of an EKG.

6. A minimally invasive method according to claim 5, wherein each of said ejection phase waveforms is determined by a time period extending from a start-of-ejection point to a dicrotic notch of said peripheral arterial pressure waveform.

7. A minimally invasive method according to claim 1, wherein said steps of recording and digitizing are performed by a computer data acquisition software via a physiological recorder and an analog/digital convertor.

8. A minimally invasive method according to claim 1, where said steps of separating are performed with a computer spreadsheet software.

9. A minimally invasive method according to claim 1, wherein said human subject's left ventricular pressure, peripheral arterial pressure, pulmonary small arterial pressure and pulmonary capillary wedge pressure are transferred to a physiological recorder by a tip micromanometer and/or fluid-filled catheters.

10. A minimally invasive method according to claim 1, wherein said patient's peripheral arterial pressure is obtained by a non-invasive equipment that can record a pressure waveform.

11. A minimally invasive method according to claim 1, wherein an arterial puncture is made in said patient in order to use means for obtaining said patient's peripheral arterial pressure.

12. A minimally invasive method according to claim 1, wherein techniques for determination of a start and an end of said ejection phase waveforms and said filling phase waveforms comprise echo-Doppler-cardiography, radionuclide angiocardiography, phonocardiography, ballistocardiography, peripheral arterial pressure waveform, pressure waveforms from right heart catheterization, pacemaker recording or ECG, or any combination thereof.

13. A minimally invasive method according to claim 1, wherein formation of said ejection and filling correlation curves and relationship thereof to said patient's ejection and filling phase waveforms of said peripheral arterial pressure waveform and said pulmonary capillary wedge pressure waveform, respectively, include mathematical formulas.

14. A minimally invasive method according to claim 1, wherein said peripheral arterial pressure waveforms are obtained from arteries including at least carotid, femoral, radial, popliteal, axillary, branchial and temporal arteries.

15. A minimally invasive method according to claim 14, wherein ejection phases of pressure waveforms of different peripheral arteries have different timing constants to match said ejection phase waveform of said left ventricular pressure waveform, due to a different distance between each peripheral artery and the aortic valve.

16. A minimally invasive method according to claim 1, wherein said sorting and standardizing of said ejection and filling correlation curves is performed in an arrangement based on sex, age, heart rate, type of disease and severity of the disease.

17. A minimally invasive method according to claim 1, wherein said method forms a part of a function of a device for displaying a loop showing a patient's left ventricular pressure to volume relationship.

* * * * *